United States Patent [19]

Hruby et al.

[11] Patent Number: 4,485,039

[45] Date of Patent: Nov. 27, 1984

[54] SYNTHETIC ANALOGUES OF α-MELANOTROPIN

[75] Inventors: Victor J. Hruby; Mac E. Hadley, both of Tucson, Ariz.; Tomi K. Sawyer, Kalamazoo, Mich.

[73] Assignee: University Patents, Inc., Norwalk, Conn.

[21] Appl. No.: 387,424

[22] Filed: Jun. 11, 1982

[51] Int. Cl.³ .......................................... C07C 103/52
[52] U.S. Cl. .......................................... 260/112.5 R
[58] Field of Search ................. 424/177; 260/112.5 R

[56] References Cited

PUBLICATIONS

Sawyer et al., *Proc. Natl. Acad. Sci USA*, 79, 1751–1755 (3/1982), Biochemistry.
*Chemical Abstracts*, 97, 1982, p. 59, Abst.No., 33522(c).
*Chemical Abstracts*, 90, 1979, p. 102, Abst. No., 16790(b).
Knittel et al., *J. Med. Chem.*, 28, 124–129, (1983).
Barth et al., *Inst. of Org. Chem. and Biochem.*, Czechaslovak Academy of Sciences, 45, 3045–3050, (1980).
Hase et al., *J.A.C.S.*, 94, 3590–3600, (1972).
Swaab et al., *Front. Hormone Res.*, 4, 177–178, (1977).
Shizume et al., *Bioassay of MSH*, 54, 553–560, (1954).
Hadley et al., *A.A.A.S.*, 213, 1025–1027, (1981).
Salomon et al., *Analytical Biochem.*, 58, 541–548, (1974).
Sawyer et al., *Proc. Natl. Acad. Sci.*, 77, (No. 10), 5754–5758, (1980).
*Cellular Receptors for Hormones and Neurotransmitters*, John Wiley and Sons Ltd., Chapter 12, (1980).
Yang et al., *Int. J. Peptide Protein Res.*, 15, 130–138, (1980).
Huntington et al., *Endocrinalogy*, 96(2), 472–479, (1974).
Schwyzer *ACTH: Swiss. Fed. Ins. Tech.*, Zurich, Switzerland Annals of N.Y. Acad. of Sci., pp. 3–26.
*Peptides of the Pars Intermedia*, Pitman Medical, 244–262, (1981).

*Primary Examiner*—Delbert R. Phillips
*Assistant Examiner*—F. T. Moezie
*Attorney, Agent, or Firm*—Marshall, O'Toole Gerstein, Murray & Bicknell

[57] ABSTRACT

Cyclic analogues of the tridecapeptide hormone, α-melanotropin. (α-melanocyte stimulating hormone, α-MSH), wherein a physiologically stable intramolecular interaction exists (1) between the amino acid residue at position 4 and an amino acid residue at position 10 or 11, and/or (2) between the amino acid residue at position 5 and an amino acid residue at position 10 or 11. Preferred analogues, e.g., [half-Cys$^4$, half-Cys$^{10}$]-α-MSH display greatly increased in vitro potency, prolongation, and resistance to enzymatic degradation.

8 Claims, No Drawings

SYNTHETIC ANALOGUES OF α-MELANOTROPIN

BACKGROUND OF THE INVENTION

The present invention relates generally to synthetic analogues of the polypeptide hormone α-melanotropin and more particularly to cyclic analogues which exhibit increased potency, prolongation and serum stability characteristics in comparison to the linear native hormone.

α-Melanotropin (α-MSH, α-melanocyte stimulating hormone) is a linear tridecapeptide synthesized and secreted by the pars intermedia of the vertebrate pituitary. By convention, the amino acid residues of this linear tridecapeptide are numbered sequentially from the amino terminal (here acetyl substituted) carbon atom through the carboxy terminal (here carboxamide terminal) as follows:

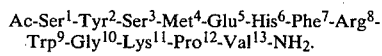

$Ac\text{-}Ser^1\text{-}Tyr^2\text{-}Ser^3\text{-}Met^4\text{-}Glu^5\text{-}His^6\text{-}Phe^7\text{-}Arg^8\text{-}Trp^9\text{-}Gly^{10}\text{-}Lys^{11}\text{-}Pro^{12}\text{-}Val^{13}\text{-}NH_2.$ In this formula the following abbreviations are used: Ser=serine; Tyr=tyrosine; Met=methionine; Glu=glutamic acid; His=histidine; Phe=phenylalanine; Arg=arginine; Trp=tryptophan; Gly=glycine; Lys=lysine; Pro=proline; Val=valine.

α-MSH reversibly darkens amphibian skins by stimulating melanosome movement (dispersion) within melanophores. α-Melanotropin also affects both normal and transformed (melanoma) mammalian melanocytes by stimulating adenylate cyclase activity, tyrosinase activity and melanin production. In addition, recent studies suggest that the native hormone may have important physiological roles in the control of vertebrate pigment cell melanogenesis (See, Hadley, et al., *Peptides of the Pars Intermedia*, 81 (Evered, et al., Eds.), 242–261, Pitman Medical, London.)) and important functions in fetal development and in neural mechanisms related to learning and memory. See, *Front. Horm. Res.*, 4, (Tilders, et al., Eds.), S. Karger, Basil (1977).

The recognition that α-MSH functions in a number of roles in mammals, including humans, in addition to its well-characterized role in the color change mechanism of poikilothermic vertebrates and its effect on melanoma cell activity and growth, has prompted substantial research into production and testing of synthetic α-MSH and analogues thereof.

Variation in biological effects of some α-MSH analogues generally can be discussed in terms of "potentiation" (increased activity relative to naturally-occurring α-MSH) and "prolongation". Such effects are measured by the classic frog skin bioassay system (See, Shizume, et al., *Endocrinology*, 54, 553–560 (1954)), or the lizard skin bioassay system (See, Hadley, et al., *Science*, 213, 1025–1027 (1981); Huntington, et al., *Endocrinology*, 66, 599–609 (1970)). Because α-MSH has an extremely short half-life in serum (less than 2 minutes), synthetic analogues having greater serum stability in addition to greater potency and prolongation characteristics have been sought.

Of particular interest to the background of the invention are studies of the structure-function relationships of α-MSH through analysis of the biological activity of a number of structurally or stereochemically modified α-MSH analogues. The amino acid residue sequences of α-MSH believed to be important for expression of melanotropic activity (the so-called "active sites") have been identified. It has been suggested that α-MSH contains two active sites, $(Glu^5)\text{-}His^6\text{-}Pre^7\text{-}Arg^8\text{-}Trp^9$ and $Gly^{10}\text{-}Lys^{11}\text{-}Pro^{12}\text{-}Val^{13}\text{-}NH_2$. See, Eberle, *Cellular Receptors for Hormones and Neurotransmitters* (Schluster, et al., Eds.), New York (1980), pp. 219–231. Each of these sequences of α-MSH can apparently stimulate melanosome dispersion in amphibian melanophores in vitro. See, Schwyzer, *Ann. N.Y. Acad. Sci.*, 217, 3–26 (1977). Studies of the biological activity of stereochemically modified α-MSH analogues of α-MSH have also provided important insights relative to the structural requirements of the native hormone for receptor binding and subsequent melanotropic expression. Substitution of the D-isomeric configuration of the amino acid residue phenylalanine at position 7 and the amino acid residue norleucine at position 4 of the native hormone has led to an α-MSH analogue $[Nle^4,D\text{-}Phe^7]\text{-}\alpha\text{-}MSH$ which exhibits significant increases in potency, prolongation and greater stability toward enzymatic degradation. See, Sawyer, et al., *P.N.A.S.*, 77, 5754–5758 (1980). Specifically incorporated by reference to illustrate the background of the invention and the prior art is the inventors' co-pending patent application Ser. No. 341,387, filed Oct. 23, 1981.

Also of interest to the background of the present invention are studies which suggest that α-MSH is a conformationally flexible linear molecule in aqueous solution. See, Schwyzer, supra. However, experimental research into the biologically active conformation of α-MSH, i.e., the three-dimensional configuration of the native hormone at the moment it is bound to its receptor and elicits signal transduction resulting in a biological response, has not been elucidated.

There continues to exist, therefore, a long-standing need in the art for physiologically stable, highly potent analogues of α-MSH which exhibit prolonged biological response and resistance to enzymatic degradation.

Specifically incorporated by reference herein for purposes of illustrating the background of the present invention and the prior art is the publication by the inventors and their co-workers appearing in *P.N.A.S.*, 79, pp. 1751–1755 (March, 1982).

BRIEF SUMMARY

The present invention provides novel synthetic analogues of α-MSH which possess an unexpected combination of high potency and prolonged activity and serum stability.

The novel compounds according to the invention comprise cyclic α-MSH analogues, wherein a physiologically stable intramolecular interaction exists between (1) the amino acid residue at the number 4 position and an amino acid residue at the 10 or 11 position, and/or (2) the amino acid residue at the 5 position and an amino acid residue at the 10 or 11 position.

Preferred compounds according to the invention include the [half-Cys$^4$, half-Cys$^{10}$] cyclic analogue of α-MSH in which the physiologically stable intramolecular interaction is a covalent disulfide bond existing between two cystine residues, one cystine residue being substituted for methionine at the "4" position, and the other cystine residue replacing glycine at the "10" position of the tridecapeptide.

Also comprehended by the invention are those analogues wherein the disulfide bond exists between cystine residues substituted at the "4" and "11", "5" and "10", or "5" and "11" positions of the tridecapeptide.

Also comprehended by the invention are bicyclic compounds wherein disulfide bonds exist between the "4" and "10" and "5" and "11" positions, or the "4" and "11" and "5" and "10" positions of the tridecapeptide.

The present invention also comprehends cyclic and bicyclic α-MSH analogues wherein the physiologically stable intramolecular interaction is a covalent carba (carbon-sulfur) or dicarba (carbon-carbon) bond.

Analogues of the invention may be readily prepared by the well-known methods used in preparing synthetic α-MSH and subsequent cyclization by methods whose exact procedures depend upon the nature of the residues substituted into the tridecapeptide and the nature of the desired physiologically stable intramolecular interaction.

Compounds of the invention are highly potent in vitro stimulators of mouse adenylate cyclase activity. The compounds are also generally more potent that α-MSH and [Nle$^4$, D-Phe$^7$]-α-MSH in the in vitro amphibian melanophore dispersion bioassay and, unlike α-MSH, exhibit prolonged biological activity in such systems. Compounds of the invention also exhibit greater resistance to enzymatic degradation than α-MSH.

Numerous aspects and advantages of the present invention will become apparent upon consideration of the following detailed description.

DETAILED DESCRIPTION

The following examples illustrate the preparation and biological activity of cyclic α-MSH analogues wherein a physiologically stable intramolecular interaction exists (1) between the amino acid residue at position 4 and an amino acid residue at position 10 or 11, and/or (2) between the amino acid residue at position 5 and an amino acid residue at position 10 or 11.

More specifically, Examples 1 through 6 illustrate the preparation of [half-Cys$^4$, half-Cys$^{10}$]-α-MSH and acetyl-[half-Cys$^4$, half-Cys$^{10}$]-α-MSH$_{4-13NH2}$ and the testing of their biological properties.

EXAMPLE 1

[Half-Cys$^4$, half-Cys$^{10}$]-α-MSH and acetyl-[half-Cys$^4$, half-Cys$^{10}$]-α-MSH$_{4-13NH2}$ were synthesized by solid phase synthesis and purified according to the method described in Sawyer et. al., *P.N.A.S.*, 79, pp. 1751-1755 (1982).

Briefly summarized, the compounds were synthesized by first preparing a p-methylbenzhydrylamine resin to which the desired amino acids were coupled successively as their N$^\alpha$-Boc derivatives. Except for use of cystine as a substitute for methionine at position 4 and for glycine at position 10, all amino acid residues used in [half-Cys$^4$, half-Cys$^{10}$]-α-MSH were identical to those present in native α-MSH. In the preparation of acetyl-[half-Cys$^4$, half-Cys$^{10}$]-α-MSH$_{4-13NH2}$, of course, the initial three amino acids of the native hormone were not added. The reactive side group of each amino acid was protected by incorporation of an appropriate protective group, if needed. After all the amino acid residues were coupled to the resin, the amino terminus of the peptide-resin was acetylated. Subsequent to acetylation the protected peptide was cleaved from the resin, and all protecting groups were removed by HF. The fully deprotected peptides were then cyclized by oxidation of the cystine residue side groups. The crude products were purified by ion-exchange chromatography and gel filtration and homogeneity was tested by thin layer chromatography on silica gel using appropriate solvents. Optical rotation values were measured at the mercury-green line (546 nm) in a Perkin-Elmer 241 MC polarimeter.

The following examples illustrate the enhanced potency of the compounds of Example 1 on the in vitro amphibian skin melanophore dispersing assay. The α-MSH utilized for comparative purposes in this and subsequent examples was prepared as described in Yang, et al., *Int. J. Pept. Protein Res.*, 15, 130–138 (1980).

EXAMPLE 2

The Example 1 compounds were examined for their biological effects on melanosome dispersion in vitro using the standard frog (*Rana pipiens*) skin bioassay and photo-reflectance methods. See, Hadley, et al., *Science*, 213, pp. 1025–1027 (1981).

Both analogues exhibited a potency of over 10,000 times greater than native α-MSH in this system.

The following Example illustrates the in vitro melanosome dispersion effects of Example 1 compounds on the in vitro lizard (*Anolis carolinensis*) skin assay.

EXAMPLE 3

The biological activity of the compounds of Example 1 relative to their ability to stimulate melanosome dispersion in vitro was examined using the lizard (*Anolis carolinensis*) skin bioassay. See, Hadley, et al., *Science*, 13, pp. 1025–1027 (1981).

[Half-Cys$^4$, half-Cys$^{10}$]-α-MSH exhibited approximately thirty times more potency that the native hormone in this system, while acetyl-[half-Cys$^4$, half-Cys$^{10}$]-α-MSH$_{4-13NH2}$ was about 1.6 times as potent.

The following Example illustrates the in vitro prolonged biological activity of Example 1 compounds.

EXAMPLE 4

The compounds of Example 1 were examined with respect to the duration of their ability to stimulate melanosome dispersion in vitro using the frog (*Rana pipiens*) skin bioassay.

At time zero, $5 \times 10^{-10}$ M of α-MSH was added to one group of frog skins and $5 \times 10^{-10}$ M of the test compounds were individually added to the second and third groups of skins. At time=60 minutes, skins were rinsed and transferred to Ringers solution.

The test compounds exhibited a maximal activity of approximately 60% at time=two hours, and marked prolongation at time=three hours. The activity of native α-MSH was completely reversed in less than three hours.

The following Example illustrates the increased activity of [half-Cys$^4$, half-Cys$^{10}$]-α-MSH on mouse melanoma adenylate cyclase assay.

EXAMPLE 5

The relative effects of α-MSH and [half-Cys$^4$, half-Cys$^{10}$]-α-MSH on mammalian melanoma adenylate cyclase activity in vitro were determined by assaying [α-$^{32}$P] ATP conversion to [$^{32}$P]cAMP in Cloudman S-91 mouse melanoma tumors as described in Sawyer, et al., *Proc. Nat. Acad. Sci. USA*, 77, 5754–5758 (1980). [$^{32}$P]cAMP was isolated, purified and detected according to Salomon, et al., *Anal. Biochem.*, 24, pp. 18–26 (1976).

[Half-Cys$^4$, half-Cys$^{10}$]-α-MSH, while exhibiting the same maximal adenylate cyclase activity as α-MSH, was approximately three times as potent as the native hormone.

The following Example illustrates the resistance of [half-Cys$^4$, half-Cys$^{10}$]-α-MSH toward enzymatic degradation.

EXAMPLE 6

The comparative enzymatic stability of [half-Cys$^4$, half-Cys$^{10}$]-α-MSH and α-MSH were examined by exposing both compounds to chymotrypsin (0.1 units/ml). α-MSH was completely degraded to a biologically inactive compound within 5 minutes. However, the cyclic analogue remained stable for a period of at least 4 hours, but was completely inactivated after 24 hours.

The foregoing Examples 2 through 6 demonstrate that one or both of the Example 1 compounds according to the present invention: (a) are more potent than the natural hormone in stimulating amphibian melanophore dispersion; (b) possess more prolonged activity to stimulate melanosome dispersion in vitro than native α-MSH; (c) possess more potent adenylate cyclase activity than native α-MSH; and (d) exhibit greater comparative resistance to enzymatic degradation than native α-MSH.

While [half-Cys$^4$, half-Cys$^{10}$]-α-MSH according to Example 1 is clearly the currently most preferred and thoroughly tested compound of the invention, it is expected that advantageous properties can be obtained for other synthetic cyclic analogues of the invention wherein cystine residues are substituted at the 4 and 11, 5 and 10, or 5 and 11 positions of the native hormone and appropriate steps are taken to form disulfide bonds. For example, the cyclic analogue [half-Cys$^5$, half-Cys$^{11}$]-α-MSH, though less potent than α-MSH in the standard frog skin assay, is enzymatically more stable than α-MSH.

Similarly, it is expected that other cyclic analogues of α-MSH wherein a physiologically stable intramolecular interaction exists through covalent bonds other than disulfide bonds will possess similar advantages in terms of biological activities. Carba and dicarba cyclic analogues can be prepared in which one or both sulfur atoms in the disulfide-linked compounds noted above is replaced by a (—CH$_2$—) group. These analogues may be prepared by incorporating amino acids of the types, NH$_2$CH(CO$_2$H)CH$_2$CH$_2$SCH$_2$CH(NH$_2$)CO$_2$H, or

NH$_2$CH(CO$_2$H)CH$_2$CH$_2$CH$_2$CH$_2$CH(NH$_2$)CO$_2$H into the peptide chain at the appropriate sequence position and then closing the rings by amide bond formation. See, e.g., Barth, et al., *Collection Czechoslov. Chem. Commun.*, 45, pp. 3045–3050 (1980); and Hase, et al., *J. Am. Chem. Soc.*, 94, pp. 3590–3600 (1972).

Carba and dicarba α-MSH analogues which may be prepared according to the foregoing procedure include the following: [half-Cys$^4$, carba-half-Cys$^{10}$]-α-MSH; [half-Cys$^4$, carba-half-Cys$^{11}$]-α-MSH; [half-Cys$^5$, carba-half-Cys$^{10}$]-α-MSH; [half-Cys$^5$, carba-half-Cys$^{11}$]-α-MSH; [carba-half-Cys$^4$, half-Cys$^{10}$]-α-MSH; [carba-half-Cys$^4$, half-Cys$^{11}$]-α-MSH; [carba-half-Cys$^5$, half-Cys$^{10}$]-α-MSH; [carba-half-Cys$^5$, half-Cys$^{11}$]-α-MSH; [carba-half-Cys$^4$, carba-half-Cys$^{10}$]-α-MSH; [carba-half-Cys$^4$, carba-half-Cys-$^{11}$]-α-MSH; [carba-half-Cys$^5$, carba-half-Cys$^{10}$]-α-MSH; and [carba-half-Cys$^5$, carba-half-Cys$^{11}$]-α-MSH.

The remarkable properties of compounds of the invention render them exceptionally useful as substitutes for α-MSH in existing diagnostic, therapeutic and basic research schemes. In the area of diagnostic procedures, it is apparent that the highly potent compounds of the invention are exceptionally well suited for use in locating and/or characterizing melanoma cells on the basis of association with melanotropin receptors in such cells. The serum stability of compounds of the invention makes them prime candidates in proposed selective drug delivery systems wherein target tissues are known to have high concentrations of melanotropin receptors. The relative high potency and prolonged activity of compounds of the invention in color change-associated phenomena is expected to be duplicated in the context of other biological effects (such as central nervous system effects) previously noted for naturally occurring melanocyte stimulating hormone and its synthetic analogues.

Numerous modifications and variations of the invention as illustrated in the above Examples are expected to occur to those skilled in the art. As one example, the above detailed description illustrates preparation and testing of an α-MSH analogue wherein a disulfide bond links amino acid residues in positions 4 and 10 and wherein the first three sequences of the native amino acid sequence for α-MSH are omitted. Similar omissions of the initial amino acids may be made in cyclic compounds of the invention including disulfide links between amino acids at positions 4 and 11, 5 and 10, and 5 and 11 (i.e., acetyl-[half-Cys$^4$, half-Cys$^{10}$]-α-MSH$_{4\text{-}13NH_2}$; acetyl-[half-Cys$^5$, half-Cys$^{10}$]-α-MSH$_{5\text{-}13NH_2}$; etc.), in bicyclic compounds, and in cyclic compounds including carba (carbon-sulfur) and dicarba (carbon-carbon) links.

What is claimed is:

1. Cyclic α-melanotropin stimulating hormone analogues wherein a physiologically stable intramolecular interaction exists (1) between the amino acid residue at position 4 and an amino acid residue at position 10 or 11, and/or (2) between the amino acid residue at position 5 and an amino acid residue at position 10 or 11.

2. Cyclic analogues according to claim 1 wherein a physiologically stable intramolecular interaction present is a covalent bond.

3. Cyclic analogues according to claim 2 wherein the covalent bond is a disulfide bond.

4. Cyclic analogues according to claim 2 wherein the covalent bond is a carba bond.

5. Cyclic analogues according to claim 2 wherein the covalent bond is a dicarba bond.

6. Cyclic α-melanotropin stimulating hormones of the formula:

[half-Cys$^4$, half-Cys$^{10}$]-α-MSH
acetyl-[half-Cys$^4$, half-Cys$^{10}$]-α-MSH$_{4\text{-}13NH_2}$
[half-Cys$^4$, half-Cys$^{11}$]-α-MSH
acetyl-[half-Cys$^4$, half-Cys$^{11}$]-α-MSH$_{4\text{-}13NH_2}$
[half-Cys$^5$, half-Cys$^{10}$]-α-MSH
acetyl-[half-Cys$^5$, half-Cys$^{10}$]-α-MSH$_{5\text{-}13NH_2}$
[half-Cys$^5$, half-Cys$^{11}$]-α-MSH
acetyl-[half-Cys$^5$, half-Cys$^{11}$]-α-MSH$_{5\text{-}13NH_2}$
[half-Cys$^4$, half-Cys$^{10}$][half-Cys$^5$, half-Cys$^{11}$]-α-MSH
acetyl-[half-Cys$^4$, half-Cys$^{10}$][half-Cys$^5$, half-Cys$^{11}$]-α-MSH$_{4\text{-}13NH_2}$
[half-Cys$^4$, half-Cys$^{11}$][half-Cys$^5$, half-Cys$^{10}$]-α-MSH
acetyl-[half-Cys$^4$, half-Cys$^{11}$][half-Cys$^5$, half-Cys$^{10}$]-α-MSH$_{4\text{-}13NH_2}$.

7. Cyclic α-melanotropin stimulating hormones of the formula:

[half-Cys$^4$, carba-half-Cys$^{10}$]-α-MSH
[half-Cys$^4$, carba-half-Cys$^{11}$]-α-MSH
[half-Cys$^5$, carba-half-Cys$^{10}$]-α-MSH
[half-Cys$^5$, carba-half-Cys$^{11}$]-α-MSH
[carba-half-Cys$^4$, half-Cys$^{10}$]-α-MSH
[carba-half-Cys$^4$, half-Cys$^{11}$]-α-MSH
[carba-half-Cys$^5$, half-Cys$^{10}$]-α-MSH
[carba-half-Cys$^5$, half-Cys$^{11}$]-α-MSH.

8. Cyclic analogues according to claim 5, namely

[carba-half-Cys$^4$, carba-half-Cys$^{10}$]-α-MSH
[carba-half-Cys$^4$, carba-half-Cys$^{11}$]-α-MSH
[carba-half-Cys$^5$, carba-half-Cys$^{10}$]-α-MSH
[carba-half-Cys$^5$, carba-half-Cys$^{11}$]-α-MSH
[carba-half-Cys$^4$, carba-half-Cys$^{10}$][carba-half-Cys$^5$, carba-half-Cys$^{11}$]-α-MSH
[carba-half-Cys$^4$, carba-half-Cys$^{11}$][carba-half-Cys$^5$, carba-half-Cys$^{10}$]-α-MSH.

* * * * *